United States Patent [19]

Tully et al.

[11] Patent Number: 5,925,520
[45] Date of Patent: Jul. 20, 1999

[54] MULTIPLEX SEQUENCING METHOD USING PRIMERS OF DIFFERENT LENGTHS TO DETECT POLYMORPHISMS

[75] Inventors: Gillian Tully; Kevin Sullivan, both of Birmingham, United Kingdom

[73] Assignee: The Secretary of State for the Home Department, Birmingham, United Kingdom

[21] Appl. No.: 08/776,944

[22] PCT Filed: Aug. 21, 1995

[86] PCT No.: PCT/GB95/01987

§ 371 Date: Feb. 14, 1997

§ 102(e) Date: Feb. 14, 1997

[87] PCT Pub. No.: WO96/06187

PCT Pub. Date: Feb. 29, 1996

[30] Foreign Application Priority Data

Aug. 25, 1994 [GB] United Kingdom ................... 9417211

[51] Int. Cl.[6] .............................. C12Q 1/68; C12P 19/34; C07H 21/04
[52] U.S. Cl. ............................ 435/6; 435/91.1; 435/91.2; 536/24.33
[58] Field of Search .............................. 435/6, 91.1, 91.2, 435/810; 536/24.33

[56] References Cited

U.S. PATENT DOCUMENTS 5,514,543  5/1996  Grossman et al. ........................ 435/6

FOREIGN PATENT DOCUMENTS

WO 92/15712  9/1992  WIPO .

OTHER PUBLICATIONS

Tully et al., Genomics 34, 107–113 (1996).
Pastinen et al., Clin. Chem. 42(9), 1391–1397 (1996).
Kobayashi et al., Mol. Cell. Probes 9, 175–182 (1995).
Juvonen et al., Hum. Genet. 93, 16–20 (1994).
Jalanko et al., Clin. Chem. 38(1), 39–43 (1992).
Kuppuswamy et al., Proc. Natl. Acad. Sci. USA 88, 1143–1147 (1991).
Syvanen et al., Genomics 8, 684–692 (1990).

*Primary Examiner*—Kenneth R. Horlick
*Attorney, Agent, or Firm*—Workman, Nydegger & Seeley

[57] ABSTRACT

A method is provided for determining the identity of at least two discrete single bases each adjacent to a predetermined nucleotide base sequence in a target sample having one or more types of polynucleotide chain. The method includes incorporating a capture group into the target sample and immobilizing the target sample by means of the capture group; mixing the target sample with (i) nucleotide primers which are complementary to predetermined base sequences such that they anneal to them at positions adjacent to the bases to be identified and (ii) at least two types of dideoxy nucleoside triphosphate (ddNTPs), each type labelled with a distinguishable fluorescent group, and (iii) a nucleotide chain extending enzyme such that ddNTPs complementary to the bases to be identified are incorporated into the nucleotide primers; eluting the extending nucleotide primers, separating the types of extended nucleotide primer on basis of size or charge and identifying the ddNTPs incorporated into each type of nucleotide primer by reference to the fluorescent characteristics associated with the distinguishable groups. Primers and a test kit are provided for use in performance of the method.

38 Claims, 3 Drawing Sheets

Fig. 1.

SCHEMATIC DIAGRAM OF MINISEQUENCING PROCESS

AMPLIFY IN TRIPLEX WITH 4 BIOTINYLATED PRIMERS + 2 NON-BIOTINYLATED PRIMERS

IMMOBILISE THE BIOTINYLATED PRODUCTS ON STREPTAVIDIN-COATED MAGNETIC BEADS

X=POLYMORPHISM

ADD MINISEQUENCING PRIMERS AND ANNEAL

...GCTAGGCTTAAGGGCTACCCAATGCATTGGCAGCTTGC..
ATCCGAATTCCCGATGGGTT    TAACCGTCGAA

ADD FLUORESCENT ddNTPs AN EXTEND ddGTP   ddATP   ddCTP

ELUTE EXTENDED MINISEQUENCING PRIMERS

ATCCGAATTCCCGATGGGTTA

TAACCGTCGAAC

ELECTROPHORESE

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 31 base pairs
      (B) TYPE: nucleic acid
      (C) STRANDEDNESS: single
      (D) TOPOLOGY: linear    (ii) MOLECULE TYPE: DNA (genomic)

(iii) HYPOTHETICAL: NO

(iii) ANTI-SENSE: NO

(vi) ORIGINAL SOURCE:
      (A) ORGANISM: Homo sapiens
      (I) ORGANELLE: Mitochondrion    (xi) SEQUENCE DESCRIPTION: SEQ ID NO: 1:

GTGCTGTGGC CAGAAGCGGG GGGAGGGGGG G                        31

(2) INFORMATION FOR SEQ ID NO: 2:

(i) SEQUENCE CHARACTERISTICS:
      (A) LENGTH: 37 base pairs
      (B) TYPE: nucleic acid
      (C) STRANDEDNESS: single
      (D) TOPOLOGY: linear    (ii) MOLECULE TYPE: DNA (genomic)

(iii) HYPOTHETICAL: NO

(iii) ANTI-SENSE: NO

(vi) ORIGINAL SOURCE:
      (A) ORGANISM: Homo sapiens
      (I) ORGANELLE: Mitochondrion    (xi) SEQUENCE DESCRIPTION: SEQ ID NO: 2:

TTTTTTTTTC CAGCGTCTCG CAATGCTATC GCGTGCA                 37

(2) INFORMATION FOR SEQ ID NO: 3:

(i) SEQUENCE CHARACTERISTICS:
      (A) LENGTH: 38 base pairs
      (B) TYPE: nucleic acid
      (C) STRANDEDNESS: single
      (D) TOPOLOGY: linear    (ii) MOLECULE TYPE: DNA (genomic)

(iii) HYPOTHETICAL: NO

(iii) ANTI-SENSE: NO

(vi) ORIGINAL SOURCE:
      (A) ORGANISM: Homo sapiens
      (I) ORGANELLE: Mitochondrion    (xi) SEQUENCE DESCRIPTION: SEQ ID NO: 3:

TTTTTTTTTT GTGCTATGTA CGGTAAATGG CTTTATGT                38

(2) INFORMATION FOR SEQ ID NO: 4:

(i) SEQUENCE CHARACTERISTICS:

(A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 4:

TTTTTTTTTT TTTTTTTAAA TACATAGCGG TTGTTGATGG GT                    42

(2) INFORMATION FOR SEQ ID NO: 5:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 5:

TTTTTTTTTT TTTTTTTCT ACGTTCAATA TTAYAGGCGA VCATAC                 46

(2) INFORMATION FOR SEQ ID NO: 6:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 6:

TTTTTTTTTT TTTTTCTGT AATATTGAAC GTAGGTGCGA TAAATAAT               48

(2) INFORMATION FOR SEQ ID NO: 7:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO

```
        (vi) ORIGINAL SOURCE:
              (A) ORGANISM: Homo sapiens
              (I) ORGANELLE: Mitochondrion (xi) SEQUENCE DESCRIPTION: SEQ ID NO: 7:

TTTTTTTTTT TTTTTTTTTT TTTTGTCGCA GTATCTGTCT TGATTCCTR CC            52

(2) INFORMATION FOR SEQ ID NO: 8:

(i) SEQUENCE CHARACTERISTICS:
              (A) LENGTH: 54 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iii) ANTI-SENSE: NO (vi) ORIGINAL SOURCE:
              (A) ORGANISM: Homo sapiens
              (I) ORGANELLE: Mitochondrion (xi) SEQUENCE DESCRIPTION: SEQ ID NO: 8:

TTTTTTTTTT TTTTTTTTTT TTTTTTCTGT GTGGAAAGTG GCTGTGCAGA CATT          54

(2) INFORMATION FOR SEQ ID NO: 9:

(i) SEQUENCE CHARACTERISTICS:
              (A) LENGTH: 56 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iii) ANTI-SENSE: NO (vi) ORIGINAL SOURCE:
              (A) ORGANISM: Homo sapiens
              (I) ORGANELLE: Mitochondrion (xi) SEQUENCE DESCRIPTION: SEQ ID NO: 9:

TTTTTTTTTT TTTTTTTTTT TTTTTTTTTG GAGTTGCAGT TGATGTGTGA TAGTTG        56

(2) INFORMATION FOR SEQ ID NO: 10:

(i) SEQUENCE CHARACTERISTICS:
              (A) LENGTH: 63 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iii) ANTI-SENSE: NO (vi) ORIGINAL SOURCE:
              (A) ORGANISM: Homo sapiens
              (I) ORGANELLE: Mitochondrion (xi) SEQUENCE DESCRIPTION: SEQ ID NO: 10:

TTTTTTTTTT TTTTTTTTTC TCATCAATAC AACCCCCGCC CATCCTACCC AGCACACACA    60
CAC                                                                  63
```

(2) INFORMATION FOR SEQ ID NO: 11:

(i) SEQUENCE CHARACTERISTICS:
        (A) LENGTH: 66 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iii) ANTI-SENSE: NO

(vi) ORIGINAL SOURCE:
        (A) ORGANISM: Homo sapiens
        (I) ORGANELLE: Mitochondrion     (xi) SEQUENCE DESCRIPTION: SEQ ID NO: 11:

```
TTTTTTTTTT TTTTTTTTTT TTTTCTCATC AATACAACCC CCGCCCATCC TACCCAGCAC      60

ACACAC                                                                 66
```

(2) INFORMATION FOR SEQ ID NO: 12:

(i) SEQUENCE CHARACTERISTICS:
        (A) LENGTH: 70 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iii) ANTI-SENSE: NO

(vi) ORIGINAL SOURCE:
        (A) ORGANISM: Homo sapiens
        (I) ORGANELLE: Mitochondrion     (xi) SEQUENCE DESCRIPTION: SEQ ID NO: 12:

```
TTTTTTTTTT TTTTTTTTTT TTTTTTTTTT TTTTTTTTTT GTACTACAGG TGGTCAAGTA      60

TTTATGGTAC                                                             70
```

(2) INFORMATION FOR SEQ ID NO: 13:

(i) SEQUENCE CHARACTERISTICS:
        (A) LENGTH: 75 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iii) ANTI-SENSE: NO

(vi) ORIGINAL SOURCE:
        (A) ORGANISM: Homo sapiens
        (I) ORGANELLE: Mitochondrion     (xi) SEQUENCE DESCRIPTION: SEQ ID NO: 13:

```
TTTTTTTTTT TTTTTTTTTT TTTTTTTTTT TTTTTTTTTT TTGGTTGATT GCTGTACTTG      60

CTTGTAAGCA TGRGG                                                       75
```

(2) INFORMATION FOR SEQ ID NO: 14:

(i) SEQUENCE CHARACTERISTICS:
        (A) LENGTH: 21 base pairs
        (B) TYPE: nucleic acid

```
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (vi) ORIGINAL SOURCE:
          (A) ORGANISM: Homo sapiens
          (I) ORGANELLE: Mitochondrion (xi) SEQUENCE DESCRIPTION: SEQ ID NO: 14:

TGCATTTGGT ATTTTCGTCT G                                              21

(2) INFORMATION FOR SEQ ID NO: 15:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (vi) ORIGINAL SOURCE:
          (A) ORGANISM: Homo sapiens
          (I) ORGANELLE: Mitochondrion (xi) SEQUENCE DESCRIPTION: SEQ ID NO: 15:

CAGAGATGTG TTTAAGTGCT GT                                             22

(2) INFORMATION FOR SEQ ID NO: 16:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (vi) ORIGINAL SOURCE:
          (A) ORGANISM: Homo sapiens
          (I) ORGANELLE: Mitochondrion (xi) SEQUENCE DESCRIPTION: SEQ ID NO: 16:

GAACCCTAAC ACCAGCCTAA C                                              21

(2) INFORMATION FOR SEQ ID NO: 17:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (vi) ORIGINAL SOURCE:
          (A) ORGANISM: Homo sapiens
```

-continued

```
        (I) ORGANELLE: Mitochondrion (xi) SEQUENCE DESCRIPTION: SEQ ID NO: 17:

GGAGGTAAGC TACATAAACT GTG                                              23

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 18:

TCATGGGGAA GCAGATTTGG                                                  20

(2) INFORMATION FOR SEQ ID NO: 19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 19:

GGATTTGACT GTAATGTGCT ATG                                              23
```

MULTIPLEX SEQUENCING METHOD USING PRIMERS OF DIFFERENT LENGTHS TO DETECT POLYMORPHISMS

This application is a 35 U.S.C. 371 of PCT/GB95/01987 filed Aug. 21, 1995.

The present invention relates to methods of nucleotide sequencing, and more particularly to methods for rapidly determining the identity of several single bases at given locations simultaneously within one or more target nucleotide base sequences within a sample comprising one or more polynucleotide chains.

BACKGROUND OF THE INVENTION

The ability to determine the identity of a nucleotide within a characterised sequence of DNA has many applications in the fields of medical and forensic science. For instance, changes in one or more individual, ie. single, bases in genomic DNA have been shown to be associated with a number of human hereditary diseases including muscular dystrophy and cystic fibrosis. The identification of such mutations at the prenatal and postnatal stages can be a valuable diagnostic tool. Similarly, the identity of single bases at several polymorphic sites in human DNA can provide an accurate method for matching forensic samples with genetic material taken from known subjects.

Methods for the detection of characterised sequences or variations are known in which the region of DNA containing the variation is first amplified by the Polymerase Chain Reaction (PCR) and the sample is then tested using immobilised oligonucleotide probes which correspond to the possible variations in the region (Saiki et al. 1989; Proc Natl Acad Sci U.S.A. 86: 6230–6234). Such methods are cumbersome because a probe is required for each possible variation, and a separate reaction must be carried out for each probe.

Methods are also known for detecting a single base variation in which first a segment of DNA is amplified by PCR using two primers, one of which has been conjugated to biotin. The resulting biotin-DNA is immobilised and used as a template for a single detection-step primer which anneals to the DNA immediately upstream of the site of the variation. The variation is then investigated using a pair of radiolabelled nucleoside triphosphates corresponding to two possible base variations. These are added to the immobilised DNA/primer mixture in the presence of a suitable polymerase.

The identity of the base variation can then be ascertained by using a scintillation counter to measure the radioactivity incorporated into the eluted detection primer. Alternatively a digoxigenin label can be used which can be detected by spectrophotometery. This method has the disadvantage that a separate incorporation experiment must be carried out for each possible variation in each variable region. By using two distinguishable radiolabels, the number of experiments can be reduced slightly. However, each variable region must still be analysed separately which makes it laborious when analysing several polymorphic sites, for instance when compiling stringent forensic data or screening for several different inherited diseases. The present inventors have now provided a method that addresses some, and in preferred forms all, of these problems.

According to a first aspect of the present invention there is provided a method for determining the identity of at least two discrete single nucleotide bases each adjacent to a predetermined target nucleotide base sequence in a target sample comprising one or more types of polynucleotide chain, the method comprising mixing the target sample with (i) nucleotide primers which are complementary to the predetermined base sequences such that they anneal thereto at positions adjacent to the bases to be identified, (ii) at least two types of chain terminator each type labelled with a characteristic fluorescent group, and (iii) a nucleotide chain extending enzyme such that terminators complementary to the bases to be identified are incorporated into the nucleotide primers; separating the types of extended nucleotide primer on basis of size and/or charge and identifying the terminators incorporated into each type of nucleotide primer by reference to its fluorescent characteristics. Using the preferred embodiments the present invention provides a method for rapidly determining several discrete bases simultaneously.

Preferably the chain terminators are dideoxynucleoside triphosphates (ddNTPs); however other terminators such as might occur to the skilled addressee eg. nucleotide analogs or arabinoside triphosphates, are also encompassed by the present invention.

Preferably the polynucleotide is DNA, however the invention could also be applied to RNA were suitable enzymes to become available. The primary requirement for the method to operate is that each of the unknown bases is adjacent to a nucleotide base sequence which is sufficiently elucidated to allow the design of a working primer i.e one which can initiate accurate template-mediated polymerisation. The term 'adjacent' in this context means one base upstream of the unknown base i.e in the 3' direction with respect to the template strand of the target DNA.

As is known, ddNTPs differ from conventional deoxynucleoside triphosphates (dNTPs) in that they lack a hydroxyl group at the 3' position of the sugar component. This prevents chain extension of incorporated ddNTPs, and thus leads to termination. Although the use of ddNTPs in conjunction with dNTPS for the sequencing of DNA chains by the Sanger-Coulson method is well documented, in the present invention ddNTPs are used without dNTPS; hence chain extension by the chain extending enzyme terminates after the addition of only one base which is complementary to the base being determined.

Each of the ddNTPs used in the present invention is labelled with a distinguishable fluorescent group, thereby allowing all possible base identities to be ascertained in a single operation. Any distinctive fluorescent label which does not interfere with the incorporation of the ddNTP into a nucleotide chain may be suitable. Dye labels having these characteristics are discussed by Lee et al. 1992; Nucleic Acids Research Vol. 20 10: 2471–2483. The fluorescently labelled nucleotides generated by the methods of the current invention can be conveniently scanned using conventional laboratory equipment, for instance the Applied Biosystems Inc. Model 373 DNA Sequencing system.

Preferably the target DNA in the sample to be investigated is first amplified by means of the Polymerase Chain Reaction (PCR) technique well known to those skilled in the art. Enriching the target DNA used in the method can provide a quicker, more accurate. template-directed synthesis by the nucleotide chain extending enzyme. Since target DNA used in the method can consist of several different regions or chains of DNA, these can potentially be generated in a single PCR step by using several different primer pairs. The invention can be carried out without any need to separate the target chains.

Preferably the target nucleotide sequence in the sample, or a corresponding nucleotide sequence derived from it (eg. by PCR) is purified before mixing with agents (i) to (iii) by incorporating a capture group into it and immobilising it through that group. By carrying out PCR with primers which have been conjugated to a capture group, a population of target DNA can be generated which can be readily immobilised onto an insoluble, solid-phase substrate adapted to complement the capture group. Alternatively the capture group can be annealed to the target DNA directly. Any pair of chemical species which bind strongly, and one of which can be annealed to nucleotide chains, can be used. Suitably the biotin/avidin pair can be employed, with the biotin being annealed to the target DNA and the avidin being attached to a solid substrate eg. latex or polystyrene coated magnetic beads.

Immobilisation greatly facilitates the efficient removal of unincorporated primers and labelled ddNTPs, which will in turn improve the analysis of the extended primers to see which ddNTPs have been incorporated into them. This is particularly important when the invention is being applied to identify a large number of nucleotide bases in a single operation and hence where there will be many extended primer products to separate and analyse.

The number of types ddNTP which are used in the method will depend on the number of possible identities which the bases to be determined could possess. Thus, for instance, if none of the bases to be determined is likely to be an adenosine residue, then ddTTP can be omitted from the reaction mixture. In most cases, however, it will be preferable to have four ddNTP species present, so as to be able to accurately detect all possible combinations.

The nucleotide chain extending enzyme is preferably a DNA polymerase, or viable fragment thereof (such as the Klenow fragment). Most preferably the DNA polymerase is a thermostable polymerase, such as that from Thermus aquaticus ('Taq polymerase').

DETAILED DESCRIPTION OF THE INVENTION

After the incorporation of the ddNTPs, the extended nucleotide primers are preferably separated by gel electrophoresis. This facilitates the identification of the incorporated ddNTPs since the bands on the gel can be conveniently scanned with a fluorimeter set to suitable excitation/emission wavelengths. Alternatively, the primers can be separated by column chromatography such as gel filtration, and the fluorescence characteristics can be assessed by analysis of the eluent.

The nucleotide primers, which form a further aspect of this invention, should be selected such that they do not inhibit each other when used simultaneously. Preferably each primer has a length that ensures its extension product's mobility (eg. on PAGE) is distinct from other primer products. In order to facilitate separation of the extended nucleotide primers, it may be preferable to adapt the size of the nucleotide primers used in the reaction i.e. to engineer them such that they are separable by the chosen method. This is especially important when using a large number of primers to investigate several sites simultaneously. Any means which alters the size, and hence mobility, of the primer without interfering with its binding and chain initiating properties would be suitable.

Most preferably, however, the mobility is adapted by means of a polynucleotide tail attached to the 5' end of the nucleotide primer, and not being complementary to the strand being probed. The nature of the tail should be such that it causes minimal interference with the target DNA or with the rest of the primer or other primers, for instance by causing the formation of secondary or higher structures such as hairpin loops. Also it is preferable that the tail be storage-stable eg. it does not readily hydrolyse in solution. Particularly effective are polyT or polyA tails.

In a second aspect the invention makes available a method for screening a DNA sample for a plurality of genetic disorders comprising carrying out a method as herein before described, wherein the discrete single nucleotide bases being analysed are associated with genetic disorders.

Disorders which are associated with base substitution are particularly suitable for investigation by the current methods as they lead to changes which are readily identifiable. Defects such as base deletion can also be investigated if the deletion leads to a change in the identity of the base at a given position i.e. if the 'following' base is different to the one that is deleted. More complex changes, for instance oligo (G) length made available by the present invention simply by careful selection of the primers used.

In a further aspect the invention makes available a method for rapid typing of a DNA sample comprising carrying out a method as described above on a number of discrete single nucleotide bases in that sample, the bases being known to show significant variation within the population from which the sample was drawn ('forensic typing').

In a still further aspect the invention makes available a method for comparing corresponding discrete single nucleotide bases in a first DNA sample with a second DNA sample comprising carrying out a method as described above on each sample and comparing the results obtained therefrom ('forensic matching'). Under many circumstances it will be desirable to amplify the two samples by PCR—preferably this should be carried out using the same types of primer for each.

Such methods have wide application in the forensic sciences, as well as being useful research tools. The number of bases examined should be chosen according to the application, since a larger number of bases will give a more stringent test but will be more expensive to carry out. Preferably the target samples analysed in these methods comprise hypervariable segments of DNA i.e. sites at which the bases vary widely within a population. Analysis of such sites is more likely to show up differences between samples than comparison of more conserved regions.

When using the method for typing or matching of samples of human origin, the single nucleotide bases being compared are preferably at polymorphic sites in human mitochondrial or chromosomal DNA. For instance, the multiplex analysis of bi-allelic loci is particularly useful for human identification purposes.

Most preferably, forensic typing or matching is carried out on some or all of the bases at any of the following positions on the human mitochondrial genome, each of which has a characterised polymorphism associated with it: L00073 substitution, L00146 substitution, L00152 substitution, L00195 substitution, L00247 substitution, the dinucleotide repeat around L00525, L16069 substitution, L16129 substitution, L16189 substitution, L16224 substitution, L16311 substitution. The sequences at these positions are given in Anderson et al, (1981), Nature 290; p457 and their frequencies given in Piercy et al (1992) Int J Leg Med, 106, 85–90. The designation 'L' refers to the 'light' strand of the mitochondrial genome (as opposed to the 'heavy' or 'H' strand). The bases are numbered from 1 upwards in the 5' to 3' direction on the L strand. The simultaneous analysis of all 12 of these polymorphisms allows exceptionally rapid typing of human DNA-containing samples. Additionally, the choice of mitochondrial DNA allows the analysis of forensic samples which are severely degraded or contain low levels of chromosomal DNA such as old bones, shed hairs, old blood, old semen, and faeces.

Polymorphisms at the positions listed above are preferably investigated using respective primers that are targeted at sites on the L or H strand of mitochondrial DNA. If a mixture of primers annealing to both L and H strands are used, it will be necessary to ensure that any amplification stage employed in the process, for instance PCR, amplifies both strands of the duplex. Similarly, if immobilisation is being employed, then all the PCR products to be probed should be immobilisable.

The primers should be designed so as to readily initiate ddNTP incorporation by a nucleotide chain extending enzyme, and yet be easily separable after the elution and incorporation stages are complete. This ease of separation may be provided by altering the length of the primer as described above. Using this techniques several, and in preferred forms all 12, of the primers can be used simultaneously in a multiplex reaction giving a highly distinctive DNA 'fingerprint', with the probability of a random match between two unrelated Caucasians using all of the primers being approximately 0.09, based on published data of Piercy et al (1993).

In situations where data of even higher statistical significance is required, an additional polymorphism (L00309.1—oligo (g) length variation) can be investigated using another primer. The results of this analysis can be combined with the results of the 12-primer multiplex analysis, thereby decreasing the probability of a random match to approximately 0.05, based on the same published data.

Also provided by the present invention are primers suitable for probing the polymorphisms described above and having mobility modifying 5' tails. Preferably these tails are composed of a single type of polynucleotide, eg. polyT tails, or polyA tails. Most preferably each of the primers comprises one of the sequences of Seq ID Nos. 2–13 eg. is identical to the sequence, or is extended at the 5' end (i.e. has an extended tail). The tails in the Seq ID Nos. 2–13 are as shown in Table 1.

TABLE 1

| Seq ID No | Tail |
|---|---|
| 2 | 1–9 |
| 3 | 1–9 |
| 4 | 1–17 |
| 5 | 1–18 |
| 6 | 1–16 |
| 7 | 1–24 |
| 8 | 1–26 |
| 9 | 1–26 |
| 10 | 1–19 |
| 11 | 1–24 |
| 12 | 1–40 |
| 13 | 1–42 |

Also encompassed by the invention are primers having sequences which are mere workshop variations of Sequence ID Nos. 2–13, but which still have their utility i.e. are useful for probing the polymorphisms described above using the method of the present invention, and are readily separable when used together. For instance the polyT tails could be substituted by polyA tails. Similarly the tails could be shortened by a few bases, provided that this does not compromise their separability. Also, it is well known in the art that template-mediated primer extension may be initiated not with standing that a few bases are not perfectly base-paired; thus primers which differ from the above by only a few bases eg. 1 or 2, but which can still initiate template-mediated primer extension are also embraced by the present invention.

In a further aspect of the invention there is provided a kit for use in the analysis of DNA comprising one or more amplification primer-pairs having capture groups and being suitable for carrying out the polymerase chain reaction on DNA such as to amplify a portion of the DNA encompassing at least two of polymorphisms, together with two or more differently fluorescently labelled ddNTPs and/or two or more nucleotide primers targeted at a sequence adjacent the polymorphism from which chain extension using the ddNTPs can be initiated.

In a further aspect of the invention there is provided a kit for use in the analysis of at least two discrete single nucleotide bases in DNA sample comprising one or more amplification primer-pairs having capture groups and being suitable for carrying out the polymerase chain reaction on DNA such as to amplify a portion of the DNA encompassing the bases, together with two or more differently fluorescently labelled ddNTPs and/or two or more nucleotide primers targeted at a sequence adjacent the bases from which chain extension using the ddNTPs can be initiated.

Preferably the bases represent polymorphisms, and the DNA is human mitochondrial DNA and the primer pairs are suitable for amplifying a portion of the DNA encompassing at least two of the sites described above. Such kits allow the rapid analysis of multiple-nucleotide base variations. Preferably the targetting primers are those discussed above.

The methods and kits of the invention have wide applications in the fields of medical and forensic science, and also in applied molecular biology research, for instance in the screening of microorganisms. The speed and simplicity of carrying out the methods mean that they are well suited to being carried out by unskilled practitioners or to being automated. The facility for obtaining detailed DNA-typing information with minimal effort opens up the possibility of rapidly compiling and comparing forensic evidence from a wide range of sources in a short period of time.

The method and kits of present invention will now be described, by way of illustration only, by reference to the following example. Other embodiments falling within the scope of the invention will occur to those skilled in the art in the light of this.

FIGURES

Figure 1:
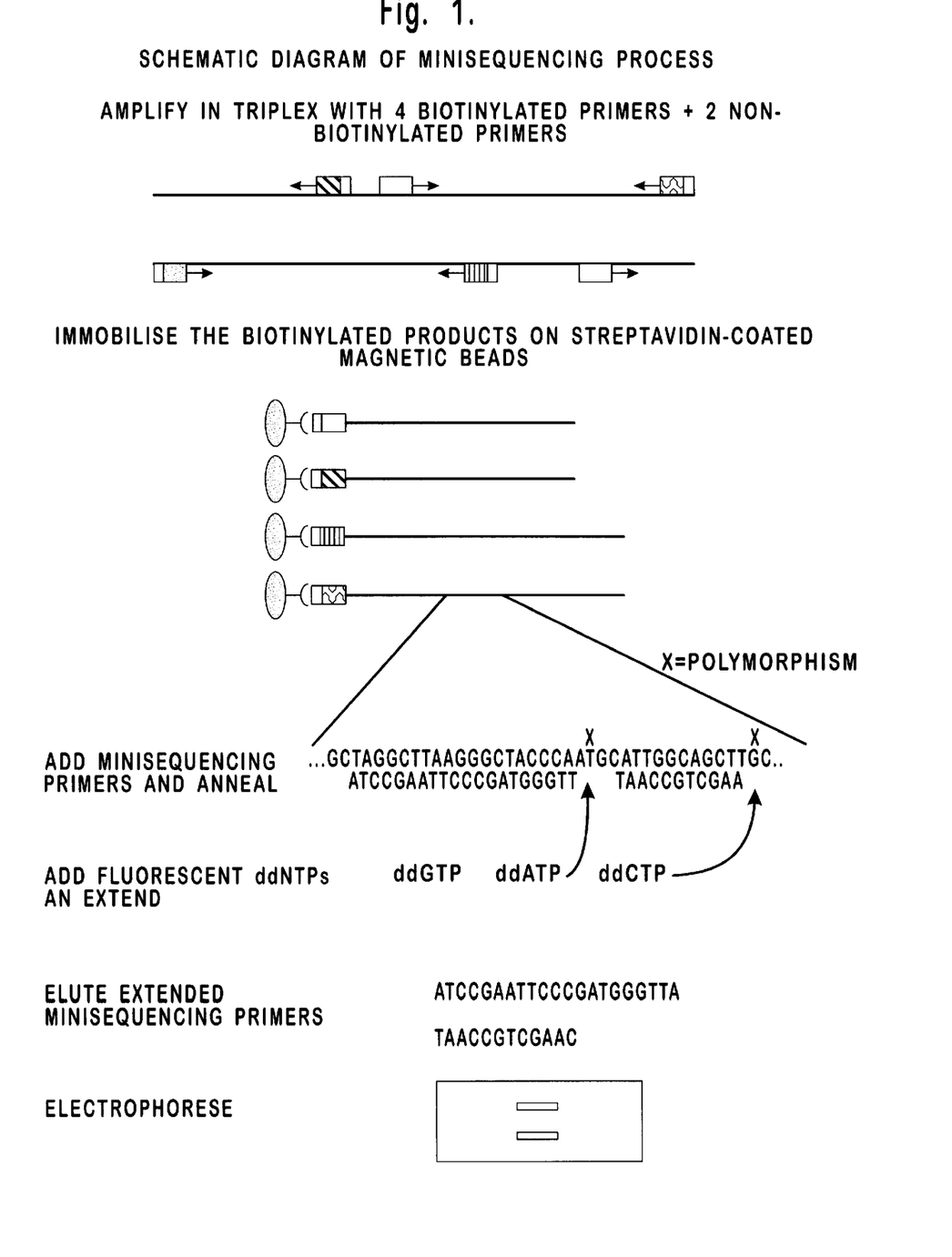
FIG. 1 shows a schematic diagram of the method described in the example.

FIG. 1 shows a schematic diagram of the method described in the Example.

Figure 2:
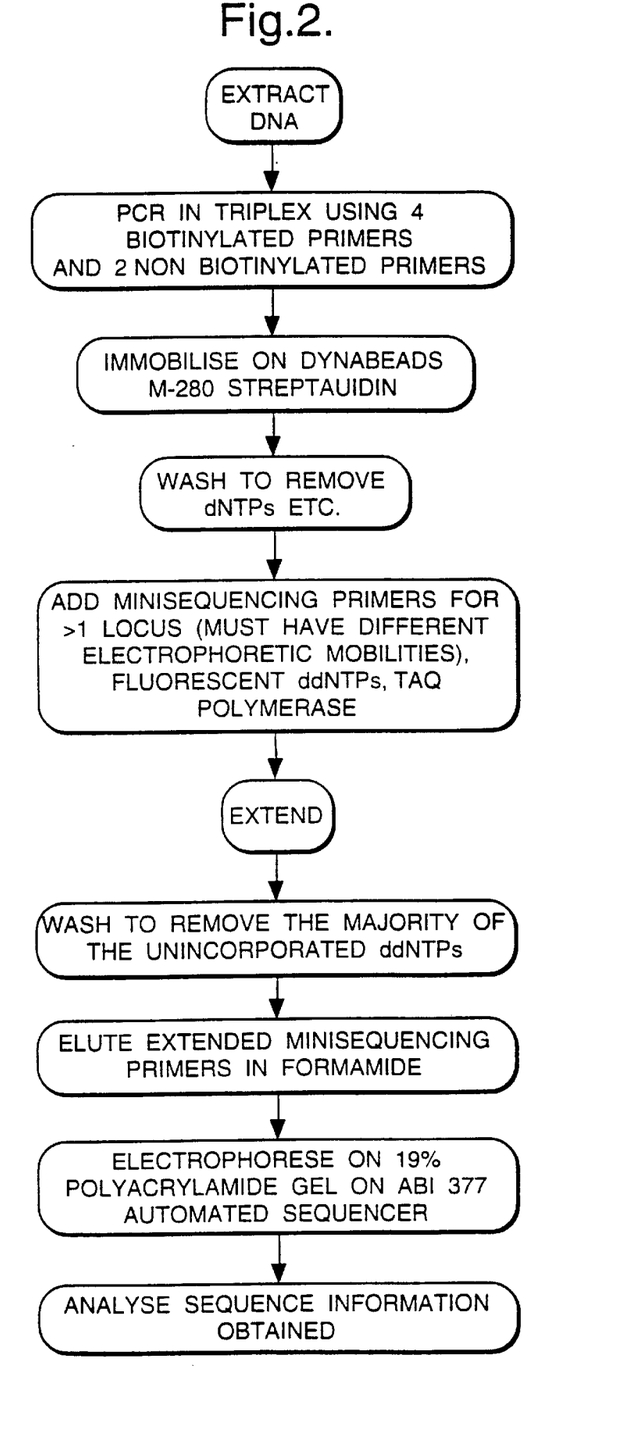
FIG. 2 shows flow chart of the steps carried out in the method described in the example.

FIG. 2 shows a flow chart of the steps carried out in the method described in the Example.

Figure 3:
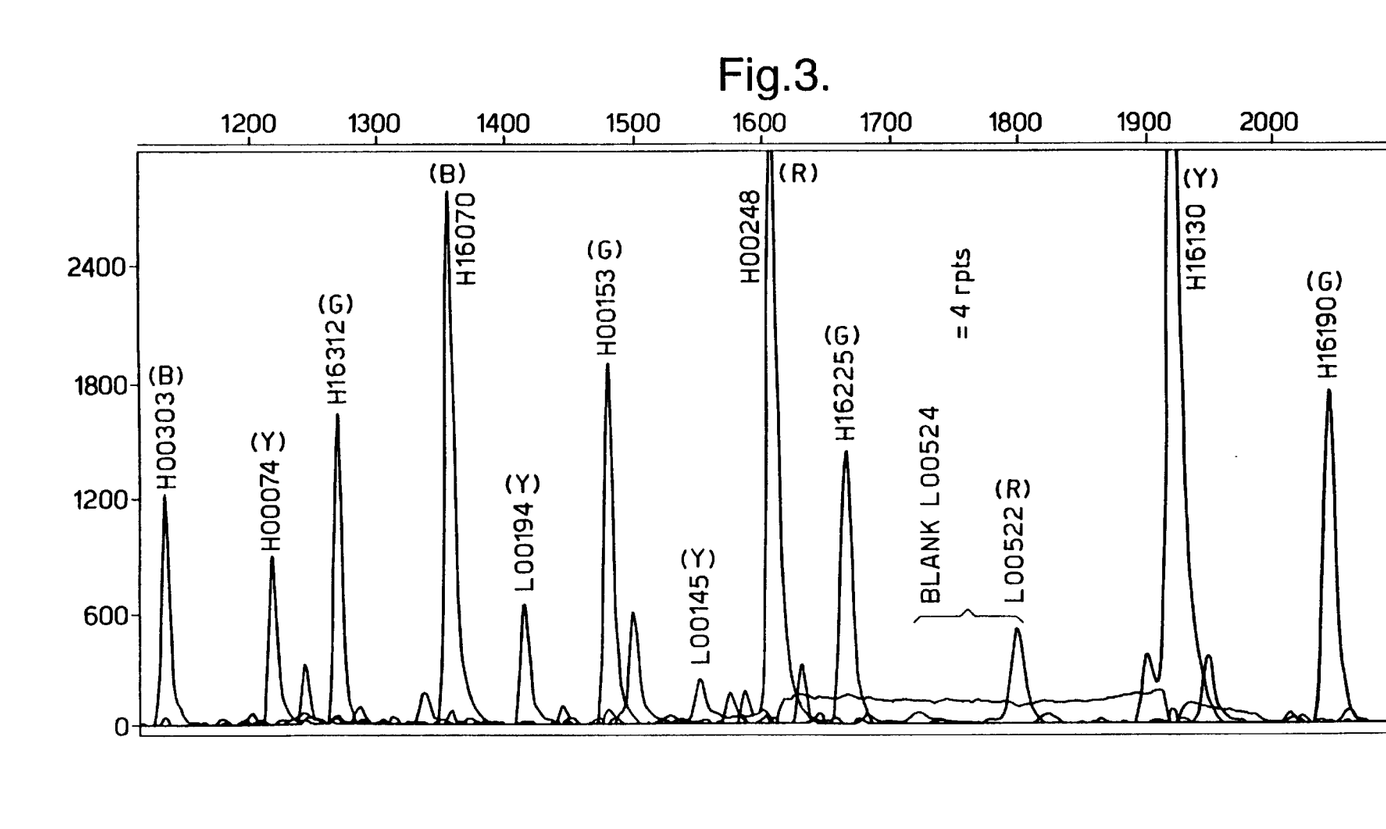
FIG. 3 shows the results obtained on a primer-extension product mix provided by carrying out the method of the example.

FIG. 3 shows the results obtained on a Genescan −672 on a primer-extension product mix provided by carrying out the method of the Example. B, G, Y and R indicate blue (G), green (A), yellow (T) and red (C) base markers.

EXAMPLE

Multiplex minisequencing of human mitochondrial genome

The principles of the method are outlined in diagram shown in FIG. 1, while a more detailed scheme is shown in FIG. 2.

Amplification of Target DNA

The regions of the mitochondrial genome between L00067 and L00325 (using SEQ ID Nos. 14 and 15), L00397 and L00572 (using SEQ ID Nos. 16 and 17), and between L16049 and L16331 (using SEQ ID Nos. 18 and 19) were amplified using a Perkin Elmer GeneAmp PCR system 9600 with 1 ng of template DNA in a total volume of 50 µl. The amplification was carried out using 35 cycles of denaturation for 30s at 94°, annealing for 30s at 57° C. and extension for 90s at 72° C. Primers corresponding to SEQ ID Nos. 14, 15, 17 and 18 had all previously been labelled with biotin at their 5' end (Oswel DNA services, Edinburgh). Concentrations used were 0.1 µM each of all primers in 1× PARR buffer (Cambio Ltd., Cambridge), 200 µM each dNTP (Boehringer Mannheim, Mannheim Germany), and 2.5 U Amplitaq DNA polymerase (Perkin Elmer Corporation, Norwalk, Conn.).

Immobilisation of Target DNA

Dynabeads M-280 Streptavidin (Dynal Oslo) were washed twice in 1× binding and washing buffer (5 mM Tris-HCl pH7.5. 0.5 mM EDTA, 1M NaCl) and resuspended in 2× binding and washing buffer containing 10% formamide. 40 µl of each PCR product was denatured at 94° C. for 1 min and snap-cooled on ice, prior to addition of 40 µl of washed beads. This mixture was incubated at 48° C. for 15 min to allow binding of the biotinylated PCR products to the streptavidin coated Dynabeads. Any remaining unbound PCR product and primers along with dNTPs from the amplification reaction were removed by 6 washes in 2× binding and washing buffer and 1 wash in sterile distilled water. Any fragments of DNA unbound to the beads but annealed to the bound PCR products were removed by incubation with 0.15M NaOH at room temperature for 4 min. followed by a wash with fresh 0.15M NaOH. 250 mM Tris-HCl pH8, 0.1% Tween20, 10 mM Tris-HCl pH7.5, 1 mM EDTA and distilled water.

ddNTP incorporation step

Minisequencing primer multimixes were prepared containing 80 mM Tris-HCl, 20 mM MgCl$_2$, 20 mM (NH$_4$)$_2$SO$_4$ 10% dimethyl sulphoxide, 0.1 µl of each fluorescent ddNTP (ddGTP, ddATP, ddTTP and ddCTP labelled with R110, R6G, 6-TAMRA and 6-ROX respectively, all supplied in solution by Applied Biosystems), 2.5 U Taq polymerase (Perkin Elmer), minisequencing primers and sterile distilled water to a total volume of 50 µl.

For the incorporation step, the distilled water was removed then the PCR product-bead complex was resuspended in 50 µl of a multimix containing 3.0 µM of primer H00303 (Seq ID No. 1). The tubes were placed in a Perkin Elmer GeneAmp PCR system 9600 thermal cycler preheated to 94° C. The temperature was immediately reduced to 52° C. and after this was attained the 50 µl of the multimix containing all the other primers, also equilibrated to this temperature, was added to the sample. The primers used in the second multimix were as shown in Table 2.

TABLE 2

Primer number gives the position adjacent the polymorphism at which the primer end base binds.

| Primer | Seq ID No | Conc. of primer (µM) |
|---|---|---|
| H00074 | 2 | 1.0 |
| H16312 | 3 | 0.66 |
| H16070 | 4 | 0.07 |
| L00194 | 5 | 0.2 |
| H00153 | 6 | 0.07 |

TABLE 2-continued

Primer number gives the position adjacent the polymorphism at which the primer end base binds.

| Primer | Seq ID No | Conc. of primer (µM) |
|---|---|---|
| L00145 | 7 | 1.3 |
| H00248 | 8 | 0.4 |
| H16225 | 9 | 0.35 |
| L00524 | 10 | 0.15 |
| L00522 | 11 | 0.03 |
| H16130 | 12 | 0.32 |
| H16190 | 13 | 0.15 |

Incubation was continued at 52° C. for 1 min before removing and placing on ice, prior to removal of the supernatent and 2 washes in 2× binding and washing buffer plus one further wash in 1× binding and washing buffer. The sample was then resuspended in deionized formamide and incubated at 72° C. for 4 min.

Separation of extended nucleotide primers: The samples were snap cooled on ice and the supernatent removed and electrophoresed for 75–90 min in a 19% polyacrylamide gel (19:1 acrylamide: bisacrylamide) using an Applied Biosystems 377 automated sequencer with a well-to-detection distance of 12 cm.

Identification of ddNTPs incorporated into primers: The results of the DNA fragment analysis by the automated sequencer are shown in FIG. 3. As can be seen the 12 peaks (plus 1 absence of peak) can be readily related to the 13 primers used in the minisequencing since the position of the peaks is dependent on the mobility, and hence the length, of the primers. The colour of the peaks corresponds to the emission wavelength of the dye-labelled ddNTP incorporated into each primer. Thus the identity of the bases on the mitochondrial sample used in the experiment can be deduced as follows (peaks being left to right i.e. shortest, most-mobile, first)

TABLE 3

Sequences of primers are as shown in Table 2.

| Peak | Primer | Colour | ddNTP | target | Base |
|---|---|---|---|---|---|
| 1 | H00303 | BLUE | G | L00302 | C |
| 2 | H00074 | YELLOW | T | L00073 | A |
| 3 | H16312 | GREEN | A | L16311 | T |
| 4 | H16070 | BLUE | G | L16069 | C |
| 5 | L00194 | YELLOW | T | L00195 | T |
| 6 | H00153 | GREEN | A | L00152 | T |
| 7 | L00145 | YELLOW | T | L00146 | T |
| 8 | H00248 | RED | C | L00247 | G |
| 9 | H16225 | GREEN | A | L16224 | T |
| — | L00524 | — | — | L00525 | } indicates |
| 10 | L00522 | RED | C | L00523 | } 4 repeats |
| 11 | H16130 | YELLOW | T | L16129 | A |
| 12 | H16190 | GREEN | A | L16189 | T |

The H Primers anneal to directly to the L strand of the mitochondrial DNA; thus the ddNTP is complementary to the base to be identified. The L primer ddNTPs have the same identity as the base to be studied. Primers L00524 and L00522 are used in conjunction to see how many repeat units are present at the locus. The blank/red result indicates 4 repeats. Other possible results are red/green (5 repeats) or green/green (6 or more repeats). The bases identified and the presence of the 4 dinucleotide repeats can be used as an accurate means of DNA typing.

We claim:

1. A method for determining the identity of at least two discrete single nucleotide bases each adjacent to a predetermined target nucleotide based sequence in a target sample comprising one or more types of polynucleotide chain, the method comprising mixing the target sample with (i) nucleotide primers which are complimentary to the predetermined base sequences such that they anneal thereto at positions adjacent to the bases to be identified, (ii) at least two types of chain terminator, each type labeled with a characteristic fluorescent group, and (iii) a nucleotide chain extending enzyme, such that terminators complimentary to the bases to be identified are incorporated into the nucleotide primers; separating the types of extended nucleotide primer according to their mobility on the basis of size or charge and identifying the terminators incorporated into each type of nucleotide primer by reference to its fluorescent characteristics wherein the size of the nucleotide primers is adapted such as to increase ease of separation of the extended nucleotide primers.

2. A method as claimed in claim 1 wherein the mobility is adapted by means of a polynucleotide tail attached to the 5' end of the nucleotide primer.

3. A method as claimed in claim 2 wherein the polynucleotide tail comprises polyA or polyT.

4. A method as claimed in any one of the preceding claims wherein the extended nucleotide primers are separated by gel electrophoresis.

5. A method as claimed in claim 1 wherein the chain terminators are dideoxynucleoside triphosphates.

6. A method as claimed in claim 5 wherein four types of dideoxynucleoside triphosphate are combined with the target sample.

7. A method as claimed in claim 1 wherein a portion of the target sample comprising the target sequences is amplified by means of the polymerase chain reaction.

8. A method as claimed in claim 1 wherein the or each nucleotide chain containing the target sequences is purified by incorporating a capture group into it and is then immobilised by means of the capture group.

9. A method as claimed in claim 8 wherein the capture group is biotin.

10. A method as claimed in claim 9 wherein the target sample is immobilised by means of streptavidin.

11. A process for producing two or more primers suitable for use in a method as claimed in claim 1 comprising:

(i) selecting two or more single nucleotide bases to be identified,
(ii) establishing the target nucleotide sequence adjacent to the bases to be identified,
(iii) synthesising primers which are complementary to the target nucleotide sequences,
(iv) adapting the relative mobility of the primers by means of a polynucleotide tail attached to the 5' end of the primer such as to increase the ease by which they can be separated from each other.

12. A process as claimed in claim 11 wherein the polynucleotide tail comprises polyA or polyT.

13. A method for screening a DNA sample for a plurality of genetic disorders comprising carrying out a method as claimed in claim 1 wherein the discrete single nucleotide bases being analysed are associated with genetic disorders.

14. A method for typing a DNA sample comprising carrying out a method as claimed in claim 1 wherein the discrete single nucleotide bases being analysed are known to show significant variation within the population from which the sample was drawn.

15. A method for comparing corresponding discrete single nucleotide bases in a first DNA sample with a second DNA sample comprising carrying out a method as claimed in claim 1 on each sample and comparing the results obtained therefrom.

16. A method as claimed in claim 14 wherein the target sample comprises hypervariable segments of DNA.

17. A method as claimed in claim 16 wherein the single nucleotide bases are at polymorphic sites in human mitochondrial or chromosomal DNA.

18. A method as claimed in claim 17 wherein the single nucleotide bases are at any of the following positions on the human mitochondrial genome: L00073, L00146, L00152, L00195, L00302, L00523, L00525, L16069, L16129, L16189, L16224, L16311.

19. A method as claimed in claim 18 wherein the single nucleotide bases are identified using one or more primers each comprising one of the nucleotide sequences designated Sequence ID Nos. 1–13 or one or more primers each comprising a nucleotide sequence differing from a nucleotide sequence designated Sequence ID Nos. 1–13 by a few bases.

20. A primer comprising one of the nucleotide sequences designated Sequence ID Nos. 2–13 or a primer comprising a nucleotide sequence deviating from the nucleotide sequences designated Sequence ID Nos. 2–13 by only a few bases.

21. A primer as claimed in claim 20 comprising one of the nucleotide sequences but wherein the tail is a polyA tail.

22. A kit for use in the analysis of polymorphic DNA comprising one or more amplification primer-pairs having capture groups and being suitable for carrying out the polymerase chain reaction on DNA such as to amplify a portion of the DNA encompassing at least two polymorphisms, together with two or more differently fluorescently labelled ddNTPs and two or more nucleotide primers targeted at a sequence adjacent respective polymorphisms from which chain extension using the ddNTPs can be initiated, the relative mobility of said primers being adapting by means of a polynucleotide tail attached to the 5' end of the primer such as to increase the ease by which they can be separated from each other.

23. A kit as claimed in claim 22 wherein the primers are produced by a process comprising:
(i) selecting two or more single nucleotide bases to be identified;

(ii) establishing the target nucleotide sequence adjacent to the bases to be identified;
(iii) synthesizing primers which are complimentary to the target nucleotide sequences; and
(iv) adapting the relative mobility of the primers by means of a polynucleotide tail attached to the 5' end of the primer such as to increase the ease by which they can be separated from each other.

24. A kit as claimed in claim 22 wherein the DNA is human mitochondrial DNA and the primer pairs are suitable for amplifying a portion of the DNA encompassing at least two mitochondrial polymorphisms.

25. A kit as claimed in claim 24 for use in the analysis of human mitochondrial DNA comprising one or more amplification primer-pairs having capture groups and being suitable for carrying out the polymerase chain reaction on human mitochondrial DNA such as to amplify a portion of the DNA encompassing at least two of the following sites: L00073, L00146, L00152, L00195, L00302, L00523, L00525, L16069, L16129, L16189, L16224, L16311 and further including primers which are immediately adjacent these sites such as to allow single base extension using fluorescently labelled ddNTPs.

26. A kit as claimed in 22 wherein the nucleotide primers comprise one or more of the nucleotide sequences designated sequence ID numbers 2–13 or one or more primers comprising a nucleotide sequence deviating from the nucleotide sequence designated sequence ID numbers 2–13 by only a few bases.

27. A method as claimed in claim 1 wherein the predetermined target sequences include at least one substitution polymorphism and at least one length polymorphism.

28. The method as claimed in claim 27 wherein the target sequence for the at least one substitutional polymorphism is selected from the group consisting of human mitochondrial genome positions L00073, L16311, L16069, L00195, L00195, L00152, L00146, L00247, L16224, L16129, and L16189 and wherein the target sequence for the at least one length polymorphism is selected from the group consisting of human mitochondrial genome positions, L00302, L00523, and L00525.

29. A method as claimed in claim 27 wherein the primer for at least one of the length polymorphisms is provided according to designated Sequence ID No. 1.

30. A method as claimed in claim 1 wherein the target sample comprises mitochondrial DNA and at least one of the predetermined target sequences is determined on one strand of the mitochondrial DNA and at least one of the predetermined target sequences is determined on the other strand of mitochondrial DNA.

31. A method as claimed in claim 30 wherein both strands of mitochondrial DNA are immobilized.

32. A method as claimed in claim 1 wherein the size of the nucleotide primers is adapted using a polynucleotide tail, the polynucleotide tail consisting of the same base throughout.

33. A method according to claim 32 wherein the polynucleotide tail consists exclusively of polyA or consists exclusively of polyT.

34. A method for determining the identity of at least two discrete single nucleotide bases, each adjacent to a predetermined target nucleotide base sequence in a target sample comprising one or more types of polynucleotides chain, the target sample comprising human mitochondrial DNA, the method comprising:
(a) mixing the target sample with (i) nucleotide primers which are complimentary to the predetermined base sequences such that they anneal thereto at positions adjacent to the bases to be identified, (ii) at least two types of chain terminator, each type labeled with a characteristic fluorescent group, and (iii) a nucleotide chain extending enzyme such that terminators complimentary to the bases to be identified are incorporated into the nucleotide primers;

(b) separating the types of extended nucleotide primer according to their mobility on the basis of size or charge and identifying the terminators incorporated into each type of nucleotide primer by reference to its fluorescent characteristics, wherein the primers anneal adjacent to at least two of the following positions on the human mitochondrial genome: L00073, L00146, L00152, L00195, L00247, L00302, L00523, L00525, L16069, L16129, L16189, L16224, L16311.

35. A method for determining the identity of at least two discrete single nucleotide bases each adjacent to a predetermined target nucleotide base sequence in a target sample comprising one or more types of polynucleotide chain, the target sample comprising mitochondrial DNA, the method comprising:

(a) mixing the target sample with (i) nucleotide primers which are complimentary to the predetermined base sequences such that they anneal thereto at positions adjacent to the bases to be identified, (ii) at least two types of chain terminator, each type labeled with a characteristic fluorescent group, and (iii) a nucleotide chain extending enzyme such that terminators complimentary to the bases to be identified are incorporated into the nucleotide primers;

(b) separating the types of extended nucleotide primer according to their mobility on the basis of size or charge and identifying the terminators incorporated into each type of nucleotide primer by reference to its fluorescent characteristics, wherein at least one of the target sequences is determined on one strand of the mitochondrial DNA and at least one of the predetermined target sequences is determined on the other strand of mitochondrial DNA.

36. A method for determining the identity of at least two discrete single nucleotide bases each adjacent to a predetermined target nucleotide base sequence in a target sample comprising one or more types of polynucleotide chain, the method comprising (a) mixing the target sample with (i) nucleotide primers which are complimentary to the predetermined base sequences such that they anneal thereto at positions adjacent to the bases to be identified, (ii) at least two types of chain terminator, each type labeled with a characteristic fluorescent group, and (iii) a nucleotide chain extending enzyme such that terminators complimentary to the bases to be identified are incorporated into the nucleotide primers;

(b) separating the types of extended nucleotide primer according to their mobility on the basis of size or charge and identifying the terminators incorporated into each type of nucleotide primer by reference to its fluorescent characteristics, wherein the predetermined target sequences include at least one substitutional polymorphism and at least one length polymorphism.

37. A primer comprising the nucleotide sequence designated Sequence ID No. 1.

38. A kit for use in the analysis of polymorphic DNA comprising one or more amplification primer-pairs having capture groups and suitable for carrying out the polymerized chain reaction on DNA such as to amplify a portion of the DNA encompassing at least two polymorphisms, together with two or more different fluorescently labeled didioxynucleicide triphosphate (ddNTPs) and two or more nucleotide primers targeted at a sequence adjacent to respective polymorphisms from which chain extension using the ddNTPs can be initiated, the relative mobility of said primers being adapted by means of a polynucleotide tail attached to the 5' end of the primers wherein the primers target a sequence adjacent at least two of the human mitochondrial genome positions L00073, L00146, L00152, L00195, L00247, L00302, L00523, L00525, L16069, L16129, L16189, L16224, L16311.

* * * * *

UNITED STATES PATENT AND TRADEMARK OFFICE
CERTIFICATE OF CORRECTION

PATENT NO. : 5,925,520
DATED : Jul. 20, 1999
INVENTOR(S) : Gillian Tully; Kevin Sullivan It is certified that error appears in the above-identified patent and that said Letters Patent is hereby corrected as shown below:

Cover Page, Abstract, lines 11 and 12, change "dideoxoy nucleoside" to
--dideoxy nucleotide--

Col. 1, line 45, after "radiolabelled" change "nucleoside" to
--dideoxy nucleotide--

Col. 2, line 16, after "are" change "dideoxynucleoside" to --dideoxy nucleotide--

Col. 2, lines 31 and 32, after "conventionally" change "deoxynucleoside" to
--dideoxy nucleotide--

Col. 5. line 28, after "this" change "techniques" to --technique--

Col. 6, line 24, after "in" insert --a--

Col. 8, line 58, after "anneal" delete "to"

Col. 20, line 52, after "are" change "dideoxynucleoside" to
--dideoxy nucleotide--

Col. 20, line 54, change "dideoxynucleoside" to --dideoxy nucleotide--

UNITED STATES PATENT AND TRADEMARK OFFICE
CERTIFICATE OF CORRECTION

PATENT NO. : 5,925,520
DATED : Jul. 20, 1999
INVENTOR(S) : Gillian Tully; Kevin Sullivan It is certified that error appears in the above-identified patent and that said Letters Patent is hereby corrected as shown below:

Col. 22, line 37, delete the second occurrence of "L00195"

Col. 22, line 62, after "types of" change "polynucleotides" to --polynucleotide--

Col. 24, lines 29 and 30, change "didioxynucleicide" to --dideoxy nucleotide--

Signed and Sealed this

Tenth Day of April, 2001

Attest:

NICHOLAS P. GODICI

Attesting Officer   Acting Director of the United States Patent and Trademark Office